US007041697B2

(12) United States Patent
Evrard et al.

(10) Patent No.: US 7,041,697 B2
(45) Date of Patent: May 9, 2006

(54) ANTIDEPRESSANT CYCLOALKYLAMINE DERIVATIVES OF 2,3-DIHYDRO-1,4-BENZODIOXAN

(75) Inventors: Deborah Ann Evrard, Hamilton Square, NJ (US); Uresh Shantilal Shah, Cranbury, NJ (US); Gary Paul Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 140 days.

(21) Appl. No.: 10/659,193

(22) Filed: Sep. 10, 2003

(65) Prior Publication Data

US 2004/0127543 A1 Jul. 1, 2004

Related U.S. Application Data

(60) Provisional application No. 60/410,169, filed on Sep. 12, 2002.

(51) Int. Cl.
*A61K 31/40* (2006.01)
*C07D 209/10* (2006.01)

(52) U.S. Cl. ...................... 514/415; 514/414; 548/507; 548/503

(58) Field of Classification Search ................. 548/507, 548/503; 514/415, 414
See application file for complete search history.

(56) References Cited

U.S. PATENT DOCUMENTS

| 5,468,767 A | 11/1995 | Cipollina et al. ............ 514/414 |
| 5,607,961 A | 3/1997 | Cipollina et al. ............ 514/415 |
| 6,410,739 B1 * | 6/2002 | Macor et al. ................ 548/181 |

FOREIGN PATENT DOCUMENTS

WO 99/51592 10/1999

OTHER PUBLICATIONS

Artigas, F., et al., "Pindolol induces a rapid improvement of depressed patients treated with serotonin reuptake inhibitors," *Arch Gen Psychiatry*, Mar. 1994, 51, 248-251.
Blier, P., et al., "Effectiveness of pindolol with selected antidepressant drugs in the treatment of major depression," *J. of Clinical Psychopharmacology*, 1995, 15(3), 217-222.
Bundgaard, (Ed.), Design of Prodrugs, *Elsevier*, 1985.
Bundgaard, H., "Means to enhance penetration; Prodrugs as a means to improve the delivery of peptide drugs," *Advanced Drug Deliver Reviews*, 1992, 8, 1-38.
Bundgaard, *J. of Pharmaceutical Sciences*, 1988, 7(285 et seq.).
Cheetham, S.C., et al., "[$^3$H]paroxetine binding in rat frontal cortex strongly correlates with [$^3$H] 5-HT uptake: effect of administration of various antidepressant treatments," *Neuropharmacol.*, 1993, 32(8), 737-743.
Eliel, E.L., Stereochemistry of Carbon Compounds, *McGraw-Hill*, NY, 1962.
Hall, M.D., et al., "{$^3$H8-hydroxy-2-(Di-n-propylamino)tetralin binding to pre- and postsynaptic 5-hydroxytryptamine sites in various regions of the rat brain," *J. Neurochem*, 1985, 44, 1685-1696.
Higuchi, et al. (Eds.), Prodrugs as Novel Drug Delivery Systems, *American Chemical Society*, 1975.
Jacques et al., Enantiomers, Racemates and Resolutions, *Wiley Interscience*, NY, 1981.
Krogsgaard-Larsen, et al. (Eds.), "Design and Application of Prodrugs," *Texbook of Drug Design and Development*, 1991, Chap. 5, 113-191.
Lazareno, S., et al., "Pharmacological characterization of acetylcholine-stimulated [$^3$S]-GTPγS binding mediated by human muscarinic m1-m4 receptors: antagonist studies," *Br. J. Pharmacol.*, 1993, 109, 1120-1127.
Perez, V., et al., "Randomised, double-blind, placebo-controlled trial of pindolol in combination with fluoxetine antidepressant treatment," *The Lancet*,m May 31, 1997, 349, 1594-1597.
Remington's Pharmaceutical Sciences, 17th Ed., Gennaro, A.R. (Ed.), Mack Publishing Company, Easton, PA, 1985.
Tome, M.B., et al., "Serotonergic autoreceptor blocade in the reduction of antidepressant latency: personality variables and response to paroxetine and pindolol," *J. Affect Disord*, 1997, 44, 101-109.
Tome, M.B., et al., "Paroxetine and pindolol: a randomized trial of serotonergic antoreceptor blockade in the reduction of antidepressant latency," *Int. Clin. Psychopharmacol*, 1997, 12, 81-89.
Widder, et al. (Eds.), Methods in Enzymology, *Academic Press*, 1985, vol. 4.
Wilen, S.H., "Tables of Resolving Agents and Optical Resolutions," *Univ. of Notre Dame Press*, Notre Dame, IN, E.L. Eliel (Ed.), 1972, p. 268-298.
Wilen, S.H., et al., "Strategies in optical resolutions," *Tetrahedron*, 1977, 33, 2725-2736.

* cited by examiner

*Primary Examiner*—Taofiq Solola
*Assistant Examiner*—Robert Shiao
(74) *Attorney, Agent, or Firm*—Woodcock Washburn LLP

(57) ABSTRACT

Compounds of the Formula I:

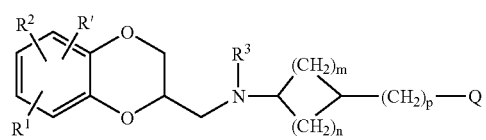

are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction and related illnesses.

27 Claims, No Drawings

ANTIDEPRESSANT CYCLOALKYLAMINE DERIVATIVES OF 2,3-DIHYDRO-1,4-BENZODIOXAN

CROSS-REFERENCE TO RELATED APPLICATIONS

This application claims the benefit of U.S. Application Ser. No. 60/410,169, filed Sep. 12, 2002, the disclosure of which is incorporated herein by reference in its entirety.

FIELD OF THE INVENTION

This invention relates to antidepressant cycloalkylamine derivatives of 2,3-dihydro-1,4-benzodioxan, to processes for preparing them, methods of using them and to pharmaceutical compositions containing them.

BACKGROUND OF THE INVENTION

Major depression is a serious health problem affecting more than 5% of the population, with a lifetime prevalence of 15–20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in less than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel antidepressant agents of the Formula I:

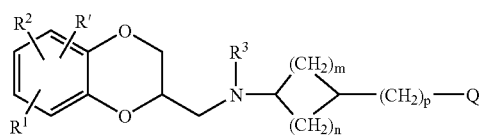

wherein

R', $R^1$ and $R^2$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$ is hydrogen or alkyl of 1 to 6 carbon atoms;

m is 1 to 3;

n is 1 or 2;

p is 0 to 3 with the proviso that when p is 0, both m and n may not be 2;

Q is a heteroaryl moiety chosen from:

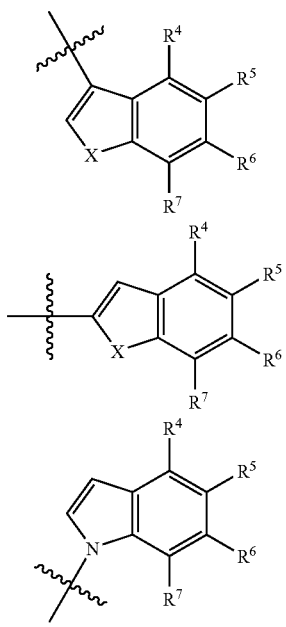

$R^4$, $R^5$, $R^6$ and $R^7$ are independently selected from hydrogen, halo, cyano, trifluoromethyl, alkyl of 1 to 6 carbon atoms, alkoxy of 1 to 6 carbon atoms, alkanoyloxy of 2 to 6 carbon atoms;

X is $NR^8$, O or S; and $R^8$ is hydrogen or alkyl of 1 to 6 carbon atoms;

or a pharmaceutically acceptable salt thereof.

Of these compounds, the preferred members are those in which $R^1$ and $R^2$ are, independently, hydrogen, halo, cyano, carboxamido, trifluoromethyl, amino, alkyl of one to six carbon atoms or alkoxy of one to six carbon atoms; $R^4$, $R^5$, $R^6$ and $R^7$ are independently hydrogen, halo, cyano, alkyl of one to six carbon atoms, or alkoxy of one to six carbon atoms; m and n are, independently, 1 or 2; p is 0 or 1, with the proviso that when p is 0, m and n may not both be 2; X and $R^8$ are defined as above.

Most preferred are those examples in which $R^1$ is alkoxy of one to six carbon atoms and is attached to position 8 of the benzodioxan moiety, $R^2$ is hydrogen, $R^4$, $R^5$, and $R^6$ and $R^7$ are independently is hydrogen, halo or cyano; m is 1; n is 2; p is 0; X is $NR^8$, and $R^8$ and $R^3$ are independently hydrogen or alkyl of 1 to 3 carbons.

Examples of Q are 3-indoles, e.g. where $R^5$ is fluoro or cyano and $R^4$, $R^6$ and $R^7$ are hydrogen.

This invention relates to both the R and S stereoisomers of the 2-aminomethyl-2,3-dihydro-1,4-benzodioxan, as well as to mixtures of the R and S stereoisomers. Throughout this application, the name of the product of this invention, where the absolute configuration of the 2-aminomethyl-2,3-dihydro-1,4-benzodioxan is not indicated, is intended to embrace the individual R and S enantiomers as well as mixtures of the two. In some embodiments of the present invention the S configuration of the 2-aminomethyl-2,3-dihydro-1,4-benzodioxan moiety is preferred.

It will be recognized that the substituents on di-substituted cycloalkyl rings may be arranged with cis or trans relative stereochemistry. It will be further recognized that when m is 1 and n is 2, the cyclopentyl moiety of the invention contains two asymmetric carbon atoms in addition to the asymmetric carbon of the 2-aminomethyl-2,3-dihydro-1,4-benzodioxan. Thus, in addition to cis and trans cyclopentylamine isomers, additional stereoisomers are possible for the cyclopentylamine moiety. This application thus encompasses all stereoisomers, individually or as mixtures, of the cycloalkylamine moiety. Furthermore, this application relates to all possible diastereomers, individually or as mixtures, of the compounds of the present invention.

Where a single stereoisomer is preferred, it may, in some embodiments be provided substantially free of the corresponding enantiomer or diastereomers. Thus, a single stereoisomer substantially free of the corresponding enantiomer or diastereomers refers to a compound which is isolated or separated via separation techniques or prepared free of the corresponding enantiomer or diastereomers. "Substantially free," as used herein, means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures or diastereomeric mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

"Alkyl," as used herein, refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

"Alkanamido," as used herein, refers to the group R—C(=O)—NH— where R is an alkyl group of 1 to 5 carbon atoms.

"Alkanoyloxy," as used herein, refers to the group R—C(=O)—O— where R is an alkyl group of 1 to 5 carbon atoms.

"Alkanesulfonamido," as used herein, refers to the group R—S(O)$_2$—NH— where R is an alkyl group of 1 to 6 carbon atoms.

"Alkoxy," as used herein, refers to the group R—O— where R is an alkyl group of 1 to 6 carbon atoms.

"Carboxamido," as used herein, refers to the group NH$_2$—C(=O)—.

"Carboalkoxy," as used herein, refers to the group R—O—C(=O)— where R is an alkyl group of 1 to 5 carbon atoms.

"Halogen" (or "halo") as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:

N-[(cis)-3-(5-fluoro-1H-indol-3-yl)cyclopentyl]-N-{[(2S)-8-methoxy-2,3-dihydro-1,4-benzodioxin-2-yl]methyl}amine;

N-[(1R,3S)-3-(5-fluoro-1H-indol-3-yl)cyclopentyl]-N-{[(2S)-8-methoxy-2,3-dihydro-1,4-benzodioxin-2-yl]methyl}amine;

N-[(1S,3R)-3-(5-fluoro-1H-indol-3-yl)cyclopentyl]-N-{[(2S)-8-methoxy-2,3-dihydro-1,4-benzodioxin-2-yl]methyl}amine;

N-[(trans)-3-(5-fluoro-1H-indol-3-yl)cyclopentyl]-N-{[(2S)-8-methoxy-2,3-dihydro-1,4-benzodioxin-2-yl]methyl}amine;

N-[(1S,3S)-3-(5-fluoro-1H-indol-3-yl)cyclopentyl]-N-{[(2S)-8-methoxy-2,3-dihydro-1,4-benzodioxin-2-yl]methyl}amine;

N-[(1R,3R)-3-(5-fluoro-1H-indol-3-yl)cyclopentyl]-N-{[(2S)-8-methoxy-2,3-dihydro-1,4-benzodioxin-2-yl]methyl}amine;

N-[(cis)-3-(5-fluoro-1-methyl-1H-indol-3-yl)cyclopentyl]-N-{[(2S)-8-methoxy-2,3-dihydro-1,4-benzodioxin-2-yl]methyl}amine;

N-[(trans)-3-(5-fluoro-1-methyl-1H-indol-3-yl)cyclopentyl]-N-{[(2S)-8-methoxy-2,3-dihydro-1,4-benzodioxin-2-yl]methyl}amine;

3-[(cis)-3-({[(2S)-8-methoxy-2,3-dihydro-1,4-benzodioxin-2-yl]methyl}amino)cyclopentyl]-1H-indole-5-carbonitrile;

3-[(trans)-3-({[(2S)-8-methoxy-2,3-dihydro-1,4-benzodioxin-2-yl]methyl}amino)cyclopentyl]-1H-indole-5-carbonitrile;

3-[(cis)-3-({[(2S)-8-methoxy-2,3-dihydro-1,4-benzodioxin-2-yl]methyl}amino)cyclopentyl]-1-methyl-1H-indole-5-carbonitrile;

3-[(trans)-3-({[(2S)-8-methoxy-2,3-dihydro-1,4-benzodioxin-2-yl]methyl}amino)cyclopentyl]-1-methyl-1H-indole-5-carbonitrile;

N-{[(2S)-8-ethoxy-2,3-dihydro-1,4-benzodioxin-2-yl]methyl}-N-[(cis)-3-(5-fluoro-1H-indol-3-yl)cyclopentyl]amine;

N-{[(2S)-8-ethoxy-2,3-dihydro-1,4-benzodioxin-2-yl]methyl}-N-[(trans)-3-(5-fluoro-1H-indol-3-yl)cyclopentyl]amine;

Compounds of the present invention are prepared in accordance with the following general description and specific examples. Variables used are as defined for Formula I, unless otherwise noted. Specifically (Scheme 1), the appropriately substituted cycloalkylamine is combined with a suitably substituted benzodioxan methyltosylate or bromide in a solvent such as dimethyl sulfoxide and heated to a temperature of 70–100° C. for several hours as illustrated below. Alternatively, the cycloalkylamine may be acylated with a suitably substituted benzodioxan carboxylic acid chloride, and the resulting amide reduced to the amine with an appropriate reducing agent such as lithium aluminum hydride or borane/THF. Alternatively, an appropriately substituted cycloalkylamine may be combined with a suitably substituted benzodioxan carboxaldehyde in the presence of a reducing agent such as sodium cyanoborohydride or sodium triacetoxyborohydride.

Scheme 1

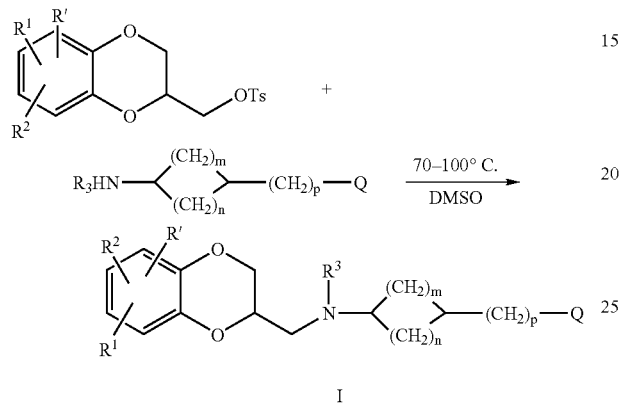

A further method of preparation is illustrated below (Scheme 2), and involves combination of a suitably substituted benzodioxanylmethylamine with the appropriate cycloalkanone in the presence of a reducing agent. Specifically, a suitably substituted benzodioxan methyltosylate or bromide is converted the corresponding azide by reaction with sodium or potassium azide in an appropriate solvent such as dimethylformamide or dimethyl sulfoxide. The azide is then conveniently reduced to the primary amine by methods known to those skilled in the art, such as hydrogenation over palladium on carbon. The amine is then combined with an appropriately substituted cyclopentanone in the presence of a reducing agent such as sodium triacetoxyborohydride or sodium cyanoborohydride to give the compounds of the invention wherein $R^3$ is hydrogen.

Scheme 2

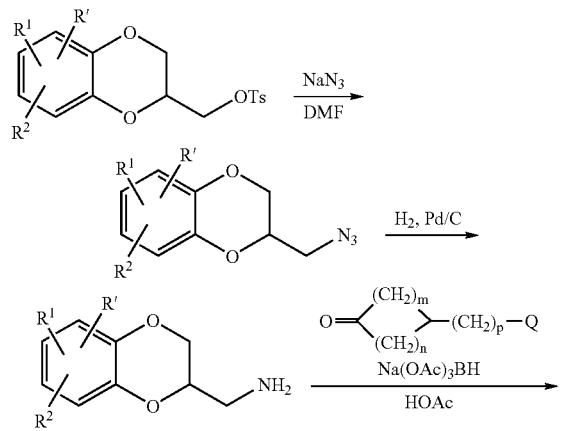

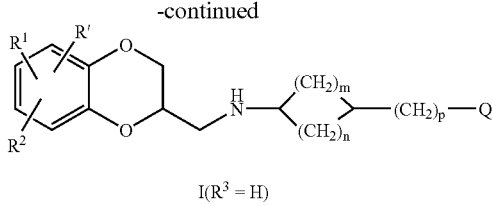

Compounds in which $R^3$ is alkyl may be prepared as in Scheme 1 above, or may be alternatively prepared from compounds of Formula I in which $R^3$ is hydrogen by reaction with a suitable aldehyde or ketone in the presence of a reduction agent such as sodium triacetoxyborohydride or sodium cyanoborohydride, as shown in Scheme 3 below.

Scheme 3

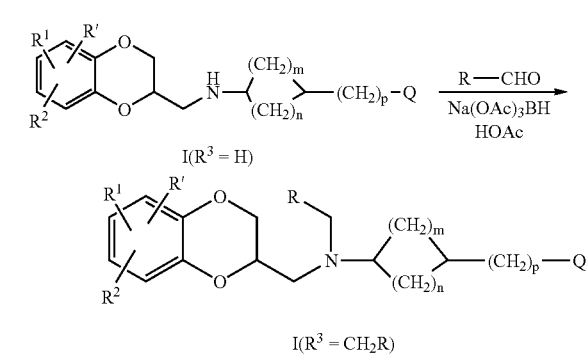

The benzodioxan methyltosylates and halides required to prepare the compounds of the invention are known compounds or they may be prepared from the appropriately substituted salicylaldehydes by the method (1) described below (Scheme 4). The salicylaldehyde is alkylated with an epihalohydrin or glycidyl arylsulfonate in the presence of a suitable base. The aldehyde moiety is then converted to a phenol by a Baeyer-Villager procedure and cyclization to the benzodioxan methanol effected by treatment with a base such as potassium carbonate. The alcohol is elaborated to a tosylate by treatment with p-toluenesulfonyl chloride and a tertiary amine base or to a bromide by treatment. Alternatively (2), the substituted salicylaldehyde may be protected with a suitable protecting group such as benzyl and the aldehyde converted to a phenol as described above. Following elaboration of the phenol to the glycidyl ether by treatment with an epihalohydrin or glycidyl arylsulfonate, deprotection and cyclization are effected in a single step via a transfer hydrogenation in the presence of sodium bicarbonate. The bromides or tosylate is prepared as described above. Or the benzodioxan methylbromide may be prepared from a suitably substituted guaiacol by procedure (3) shown above. The guiacol is alkylated with a glycidyl arylsulfonate or an epihalohydrin as described above. The methyl ether is then cleaved by treatment with 48% HBr; this also converts the epoxide to a bromohydrin. Cyclization directly to the benzodioxan methylbromide is effected by the Mitsonobu procedure. The compounds of the invention may be resolved into their enantiomers by conventional methods or, preferably, they may be prepared directly by substitution of (2R)-(−)-glycidyl 3-nitrobenzenesulfonate or tosylate (for the S benzodioxan methylamine) or (2S)-(+)-glycidyl 3-nitrobenzenesulfonate or tosylate (for the R enantiomer) in place of epichlorohydrin in the procedure above.

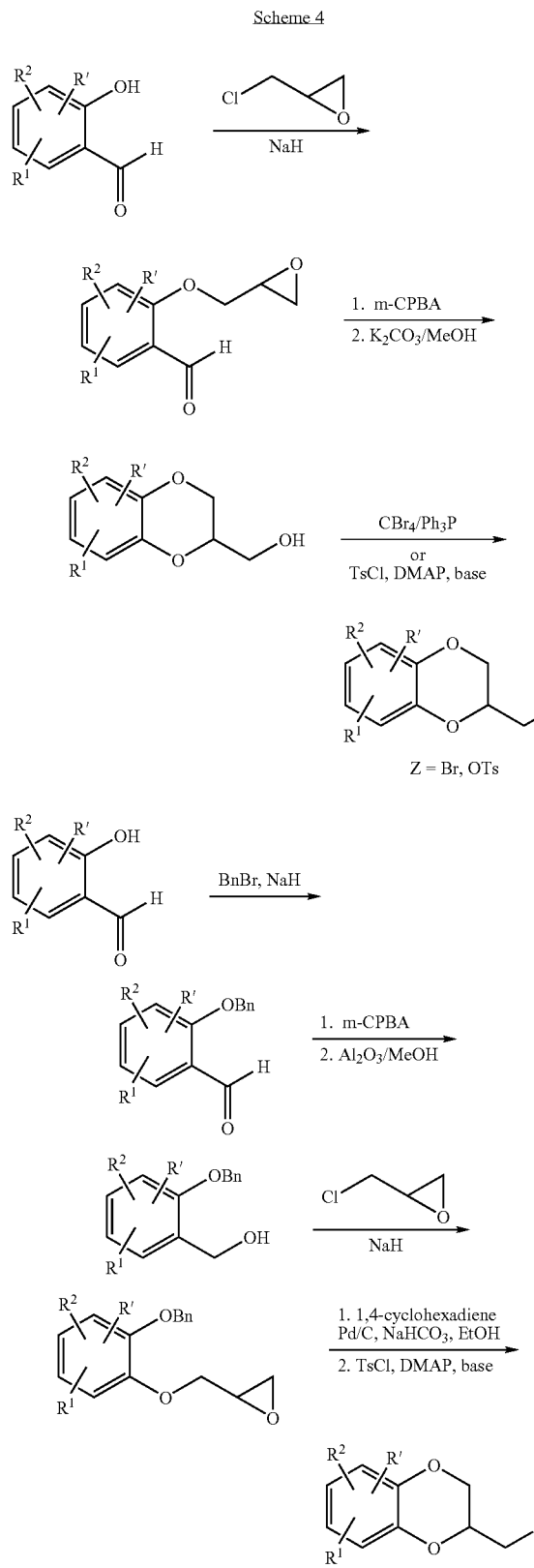

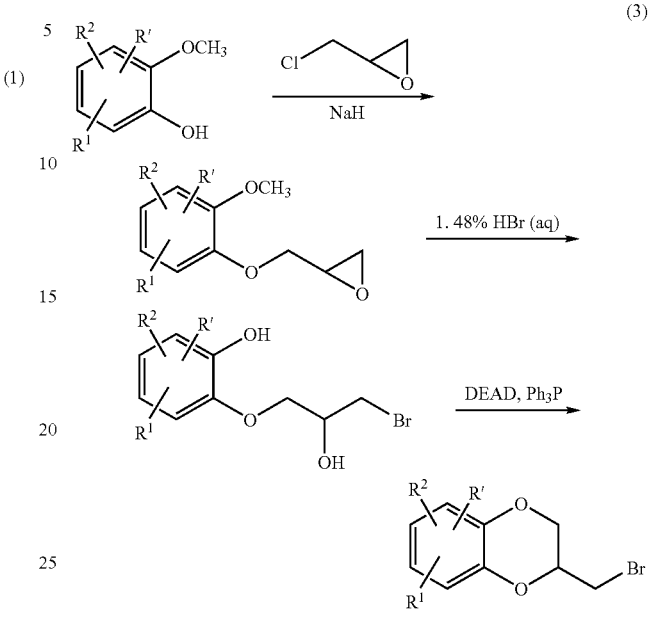

The substituted cycloalkylamines relevant to the chemistry described Scheme 1 are prepared as shown in Scheme 5. Specifically, a suitably substituted cycloalkanone is reacted with a secondary (R' is hydrogen) or tertiary amine (R' is alkyl) in the presence of a suitable reducing agent such as sodium triacetoxyborohydride or sodium cyanoborohydride to give the cycloalkyl amine. In this method the amine may be a benzodioxan methanamine as described above (Scheme 2) to give the title compounds of the invention. Alternatively, the reductive amination of Scheme 5 may produce intermediate cycloalkylamines that are then reacted with a suitably substituted benzodioxan methyltosylate or bromide as in Scheme 1 to give the title compounds of the invention.

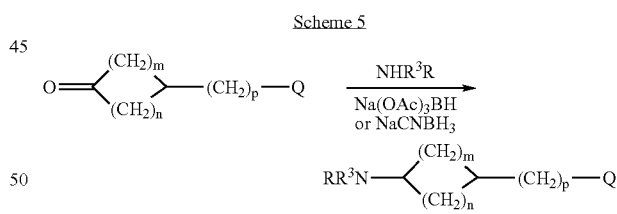

Intermediate cycloalkylamines in which $R^3$ is hydrogen are best prepared by using benzylamine (R is benzyl) in the reductive amination of Scheme 5, followed by debenzylation of the amine by transfer hydrogenation using ammonium formate and palladium on carbon in refluxing methanol (Scheme 6).

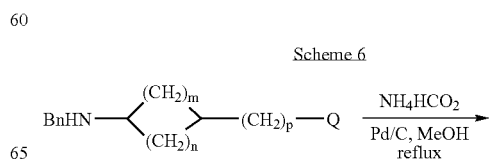

-continued

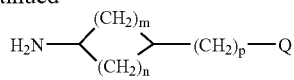

The intermediate 3-indolylcyclopentanones required for certain compounds of the invention may be prepared as shown in Scheme 7. Specifically, a suitably substituted indole is reacted with cyclopentenone in the presence of a Lewis acid to give the corresponding 3-indol-3-yl-cyclopentanone

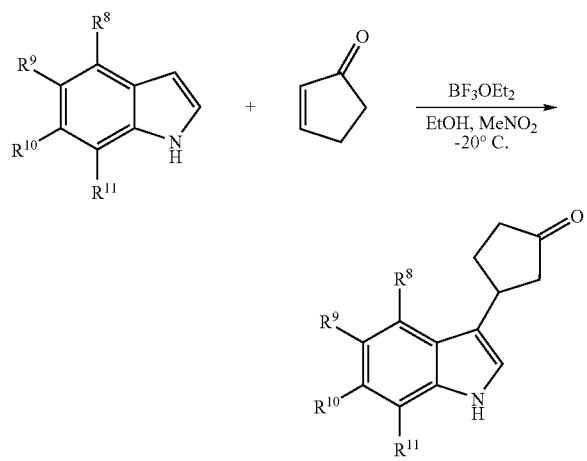

Scheme 7

A protocol similar to that used by Cheetham et al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantify bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention are reported below as $K_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the $I_{max}$, while its potency is defined by the IC$_{50}$.

The results of the three standard experimental test procedures described in the preceding three paragraphs were as follows:

| Compound | 5-HT Transporter Affinity $K_i$ (nM) | 5-HT$_{1A}$ Receptor Affinity $K_i$ (nM) | 5-HT$_{1A}$ Function IC$_{50}$ (nM) (I$_{max}$) |
|---|---|---|---|
| Example 1 | 1.07 | 5.82 | 55 (100) |
| Example 1-Isomer A | 1.28 | 7.52 | 30 (78) |
| Example 1-Isomer B | 1.92 | 3.61 | 22 (100) |
| Example 2 | 0.60 | 14.46 | 7 (99) |
| Example 2-Isomer A | 1.00 | 23.60 | 375 (84) |
| Example 2-Isomer B | 0.80 | 2.05 | 76 (32) |
| Example 3 | 12.0 | 10.75 | 152 (64) |
| Example 4 | 3.86 | 3.02 | 53 (79) |
| Example 5 | 0.60 | 8.09 | 105 (48) |
| Example 6 | 0.43 | 25.2 | 359 (25) |
| Example 7-Isomer A | 0.64 | 5.29 | nd |
| Example 7-Isomer B | 0.57 | 9.62 | 24 (56) |
| Example 8-Isomer A | 6.00 | 12.6 | EC$_{50}$ = 23 (E$_{max}$ = 64) |
| Example 8-Isomer B | 8.00 | 25.5 | nd |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorders (including but not limited to trichotillomania), obsessive compulsive spectrum disorders (including but not limited to autism), social anxiety disorder, generalized anxiety disorder, obesity, eating disorders such as anorexia nervosa and bulimia nervosa, vasomotor flushing, cocaine and alcohol addiction, sexual dysfunction (including but not limited to premature ejaculation), incontinence (including, but not limited to fecal incontinence, urge incontinence, overflow incontinence, passive incontinence, reflex incontinence, stress urinary incontinence urinary exertional incontinence and urinary incontinence), and pain (including, but not limited to migraine, chronic back pain, phantom limb pain, neuropathic pain such as diabetic neuropathy, and post herpetic neuropathy) and related illnesses. Moreover, the compounds of this invention have potent affinity for and antagonist activity at brain 5HT$_{1A}$ serotonin receptors. Recent clinical trials employing drug mixtures (eg, fluoxetine and pindolol) have demonstrated a more rapid onset of antidepressant efficacy for a treatment combining SSRI activity and 5HT$_{1A}$ antagonism (Blier and Bergeron, 1995; F. Artigas et al., 1996; M. B. Tome et al., 1997). The compounds of the invention are thus exceedingly interesting and useful for treating depressive illnesses.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions that are sterile solutions or suspensions can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I and Ia. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). *Design and Application of Prodrugs, Textbook of Drug Design and Development*, Chapter 5, 113–191 (1991), Bundgaard, et al., *Journal of Drug Deliver Reviews*, 8:1–38(1992), Bundgaard, *J. of Pharmaceutical Sciences*, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

[(2S)-8-methoxy-2,3-dihydro-1,4-benzodioxin-2-yl]-methyl amine

A mixture of (2R)-8-methoxy-2,3-dihydro-1,4-benzodioxin-2-yl]methy-4-methylbenzene-sulfonate (0.5 g, 1.43 mmol), and sodium azide (0.4 g, 6.0 mmol) in anhydrous DMF (10 mL) was stirred at room temperature for 48 hours. The reaction mixture was poured into water (50 mL) and extracted with ethyl acetate (3×50 mL). The combined organic layers were washed with water (50 mL) and brine (50 mL), then were dried over anhydrous sodium sulfate, filtered, and concentrated to give 0.4 g of the azide product as an oil, which was used without purification. To a solution of the azide (0.4 g, mmol) in THF (10 mL) was added triphenylphosphine (0.8 g, 3.05 mmol) and water (0.3 mL). The resulting mixture was stirred at room temperature for 24 hours, then was concentrated. The residue was diluted with water and extracted with ethyl acetate (3×50 mL). The combined organic layers were washed with water (30 mL) and brine (30 mL), then were dried over anhydrous sodium sulfate, filtered, and concentrated in vacuo. Flash chromatography on silica gel (20% 2 M $NH_3$ in MeOH/ethyl acetate) afforded 0.24 g (68%) of the title compound as a thick oil: MS (ESI) m/z 196 $[M+H]^+$.

Elemental Analysis for: $C_{10}H_{13}NO_3.0.5H_2O$ Calc'd: C, 58.81; H, 6.91; N, 6.86. Found: C, 59.17; H, 6.92; N, 6.57.

INTERMEDIATE 2

3-(5-Fluoro-1H-indol-3-yl)-cyclopentanone

A mixture of 5-fluoroindole (6.0 g, 44.4 mmol) and 2-cyclopenten-1-one (4.5 mL, 53.3 mmol) in nitromethane (22 mL) was cooled to −20° C. in a carbon tetrachloride-dry ice bath. A mixture of boron trifluoride etherate (1.6 mL, 11.1 mmol) and ethanol (2.2 mL, 43 mmol) was added dropwise from an addition funnel. The reaction mixture was stirred at −20° C. for 2 hours, then was quenched with 5% aqueous sodium bicarbonate solution (100 mL), and extracted with ethyl acetate (3×200 mL). The combined organic layers were washed with water (100 mL) and brine (100 mL), then were dried over anhydrous sodium sulfate, filtered and concentrated to give 9.5 g of the title compound. Trituration with ethyl acetate afforded 5.6 g (58%) of the title compound as a yellow solid. An analytical sample was recrystallized from ethyl acetate/methanol: mp 119–120° C.; MS (ESI) m/z 218 [M+H]$^+$.

Elemental Analysis for: $C_{13}H_{12}FNO$ Calc'd: C, 71.81; H, 5.57; N, 6.45. Found: C, 71.52; H, 5.41; N, 6.35.

INTERMEDIATE 3

3-(3-oxo-cyclopentyl)-1H-indole-5-carbonitrile

This compound was prepared in the same manner as for Intermediate 2, using 5-cyanoindole (4.26 g, 30 mmol) and 2-cyclopenten-1-one (2.95 g, 36 mmol) to give 5.5 g (82%) of the desired product: mp 136–138° C.; MS (ESI) m/z 224 [M]$^+$.

Elemental Analysis for: $C_{14}H_{12}N_2O$ Calc'd: C, 74.98; H, 5.39; N, 12.49. Found: C, 74.57; H, 5.29; N, 12.33.

INTERMEDIATE 4

3-(5-Fluoro-1-methyl-1H-indol-3-yl)-cyclopentanone

A suspension of sodium hydride (60% dispersion in oil, 0.335 g, 8.2 mmol) in dimethylformamide (20 mL) was stirred at room temperature. A solution of 3-(5-fluoro-1H-indol-3-yl)-cyclopentanone (1.5 g, 6.9 mmol) in 10 mL of DMF was added dropwise over 10 min. The reaction mixture was stirred at room temperature for an additional 30 min, then iodomethane (3.1 g, 21.8 mmol) was added. After stirring at room temperature for 24 hours, the reaction mixture was poured into water (100 mL) and extracted with ethyl acetate (2×100 mL). The combined organic layers were washed with water (50 mL) and brine (50 mL), then were dried over anhydrous sodium sulfate, filtered, and concentrated to give 1.6 g of crude product. Flash chromatography on silica gel (50% ethyl acetate/hexane) afforded 1.2 g (81%) of the title compound as a thick oil which solidified on standing. An analytical sample was recrystallized from ethyl acetate/hexane: mp 104–105° C.; MS (ESI) m/z 232 [M+H]$^+$.

Elemental Analysis for: $C_{14}H_{14}FNO$ Calc'd: C, 72.71; H, 6.10; N, 6.06. Found: C, 72.48; H, 5.97; N, 5.96.

INTERMEDIATE 5

1-Methyl-3-(3-oxo-cyclopentyl)-1H-indole-5-carbonitrile

This compound was prepared in the same manner as for Intermediate 4, using 3-(3-oxo-cyclopentyl)-1H-indole-5-carbonitrile (1.0 g, 4.45 mmol) to afford 0.6 g (57%) of the desired product as a white solid: mp 167–168° C.; MS (ESI) m/z 238 [M]$^+$.

Elemental Analysis for: $C_{15}H_{14}N_2O.0.1H_2O$ Calc'd: C, 75.04; H, 5.96; N, 11.67. Found: C, 74.87; H, 5.92; N, 11.59.

INTERMEDIATE 6

N-Benzyl-[3-(5-fluoro-1H-indol-3-yl)-cyclopentyl]-amine

A mixture 3-(5-fluoro-1H-indol-3-yl)-cyclopentanone (1.0 g, 4.61 mmol), benzylamine (0.54 g, 5.05 mmol) and glacial acetic acid (0.7 mL, 1.08 mmol) were stirred at room temperature for 30 min. Sodium triacetoxyborohydride (1.5 g, 7.11 mmole) was added portionwise over a 10 min period. The reaction was stirred at room temperature for 24 hours. The reaction mixture was poured into 1 N aqueous NaOH (80 mL) and extracted with ethyl acetate (3×100 mL). The combined organic layers were washed with $H_2O$ (100 mL) and brine (100 mL), then were dried over anhydrous sodium sulfate, filtered and concentrated to give 1.5 g of a thick yellow oil. Flash chromatography on silica gel (7% 2 M $NH_3$ in methanol/ethyl acetate) afforded 0.5 g of the cis isomer (first eluting) and 0.5 g of the trans isomer.

Cis isomer: MS (ESI) m/z 309 [M+H]$^+$.

Elemental Analysis for: $C_{20}H_{21}FN_2.0.50H_2O$ Calc'd: C, 75.68; H, 6.99; N, 8.83. Found: C, 75.91; H, 6.67; N, 8.70.

Trans isomer: MS (ESI) m/z 309 [M+H]$^+$.

Elemental Analysis for: $C_{20}H_{21}FN_2$ Calc'd: C, 77.89; H, 6.86; N, 9.08. Found: C, 77.22; H, 6.91; N, 9.31.

INTERMEDIATE 7

N-Benzyl-3-(5-fluoro-1-methyl-1H-indol-3-yl)-cyclopentylamine

This compound was prepared in the same manner as for Intermediate 6, using 3-(5-fluoro-1-methyl-1H-indol-3-yl)-cyclopentanone (1.25 g, 5.19 mmol) and benzylamine (0.66 g, 6.2 mmol) to afford 1.7 g of the desired product as a mixture of cis and trans isomers. Flash chromatography on silica gel (3% 2 M $NH_3$ in methanol/ethyl acetate) afforded 0.4 g (23%) of the cis isomer (first eluting) and 0.45 g (27%) of the trans isomer.

Cis Isomer: MS (ESI) m/z 323 [M+H]$^+$.

Elemental Analysis for: $C_{21}H_{23}FN_2.0.25H_2O$ Calc'd: C, 77.15; H, 7.25; N, 8.57. Found: C, 77.38; H, 7.19; N, 8.53.

Trans isomer: MS (ESI) m/z 323 [M+H]$^+$.

Elemental Analysis for: $C_{21}H_{23}FN_2.0.10H_2O$ Calc'd: C, 77.79; H, 7.21; N, 8.64. Found: C, 77.68; H, 6.99; N, 8.69.

INTERMEDIATE 8 cis-3-(5-Fluoro-1H-indol-3-yl)-cyclopentylamine

A mixture of cis-benzyl-3-(5-fluoro-1H-indol-3-yl)-cyclopentylamine (0.45 g, 1.46 mmol), 0.2 g 10% Pd/C and ammonium formate (1.0 g, 15.9 mmol) in methanol (30 mL) were refluxed under nitrogen for 4 hours. The reaction mixture was cooled, filtered through celite, and concentrated. The residue was diluted with 1 N aqueous NaOH (50 mL) and extracted with ethyl acetate (3×50 mL). The combined organic layers were washed with water (50 mL) and brine (50 mL), then were dried over anhydrous sodium sulfate, filtered and concentrated to give 0.28 g (quant.) of the title compound as a thick oil: MS (ESI) m/z 219 [M+H]$^+$.

Elemental Analysis for: $C_{13}H_{15}FN_2.0.20H_2O$ Calc'd: C, 70.37; H, 7.00; N, 12.63. Found: C, 70.65; H, 6.86; N, 12.67.

INTERMEDIATE 9 trans-3-(5-Fluoro-1H-indol-3-yl)-cyclopentylamine

This compound was prepared in the same manner as for Intermediate 8, using trans-benzyl-3-(5-fluoro-1H-indol-3-yl)-cyclopentylamine (0.45 g, 1.46 mmol) to give 0.28 g (quant.) of the title compound as a thick oil: MS (ESI) m/z 219 [M+H]$^+$.

Elemental Analysis for: $C_{13}H_{15}FN_2 \cdot 0.10H_2O$ Calc'd: C, 71.54; H, 6.93; N, 12.83. Found: C, 71.09; H, 6.67; N, 12.59.

INTERMEDIATE 10

3-cis-3-(5-Fluoro-1-methyl-1H-indol-3-yl)-cyclopentylamine

This compound was prepared in the same manner as for Intermediate 8, using cis-benzyl-3-(5-fluoro-1-methyl-1H-indol-3-yl)-cyclopentylamine (0.4 g, 1.2 mmol) to give 0.20 g (71%) of the title compound as a thick oil: MS (ESI) m/z 233 [M+H]$^+$.

Elemental analysis for: $C_{14}H_{17}FN_2 \cdot 0.25H_2O$ Calc'd: C, 71.01; H, 7.45; N, 11.83. Found: C, 70.75; H, 7.49; N, 11.61.

INTERMEDIATE 11

3-trans-3-(5-Fluoro-1-methyl-1H-indol-3-yl)-cyclopentylamine

This compound was prepared in the same manner as for Intermediate 8, using trans-benzyl-3-(5-fluoro-1-methyl-1H-indol-3-yl)-cyclopentylamine (0.42 g, 1.3 mmol), to give 0.3 g (79%) of the title compound as a thick oil: MS (ESI) m/z 233 [M+H]$^+$.

Elemental Analysis for: $C_{14}H_{17}FN_2 \cdot 0.25H_2O$ Calc'd: C, 71.01; H, 7.45; N, 11.83. Found: C, 71.14; H, 7.52; N, 11.67.

EXAMPLE 1

N-[(cis)-3-(5-fluoro-1H-indol-3-yl)cyclopentyl]-N-{[(2S)-8-methoxy-2,3-dihydro-1,4-benzodioxin-2-yl]methyl}amine A mixture of [(2R)-8-methoxy-2,3-dihydro-1,4-benzodioxin-2-yl]methyl 4-methylbenzene-sulfonate (0.5 g, 1.42 mmole) and cis-3-(5-fluoro-1H-indol-3-yl)-cyclopentylamine (0.24 g, 1.1 mmol) in anhydrous DMSO (10 mL) was heated at 80° C. for 30 h. The cooled reaction mixture was poured into 1 N aqueous NaOH (50 mL) and extracted with ethyl acetate (3×50 mL). The combined organic layers were washed with water (50 mL) and brine (50 mL), then were dried over anhydrous sodium sulfate, filtered, and concentrated in vacuo to give 0.5 g of crude product. Flash chromatography on silica gel (10% MeOH/ethyl acetate) afforded 0.2 g (48%) of the title compound as a thick oil, which was converted to its hydrochloride salt (0.195 g): MS (ESI) m/z 397 [M+H]$^+$.

Elemental Analysis for: $C_{23}H_{25}FN_2O_3 \cdot HCl$ Calc'd: C, 63.81; H, 6.05; N, 6.47. Found: C, 63.66; H, 5.98; N, 6.47.

The diastereomers of a 120 mg sample of the above compound were separated by preparative chiral HPLC (Chiralpak AD 25×2 cm, ethanol).

Isomer A: $R_T$=7.26 min: N-[(1R*,3S*)-3-(5-fluoro-1H-indol-3-yl)cyclopentyl]-N-{[(2S)-8-methoxy-2,3-dihydro-1,4-benzodioxin-2-yl]methyl}amine was converted to its hydrochloride salt (off-white solid): $[\alpha]_D$ −44.95° (c 1.0, MeOH); MS (ESI) m/z 397 [M+H]$^+$.

Isomer B: $R_T$=9.98 min: N-[(1S*,3R*)-3-(5-fluoro-1H-indol-3-yl)cyclopentyl]-N-{[(2S)-8-methoxy-2,3-dihydro-1,4-benzodioxin-2-yl]methyl}amine was converted to its hydrochloride salt (beige solid): $[\alpha]_D$ −46.04° (c 1.0, MeOH); MS (ESI) m/z 397 [M+H]$^+$.

EXAMPLE 2

N-[(trans)-3-(5-fluoro-1H-indol-3-yl)cyclopentyl]-N-{[(2S)-8-methoxy-2,3-dihydro-1,4-benzodioxin-2-yl]methyl}amine This compound was prepared in the same manner as for Example 1, using trans-3-(5-fluoro-1H-indol-3-yl)-cyclopentylamine to give 0.16 g (40%) of the title compound as its hydrochloride salt: MS (ESI) m/z 397 [M+H]$^+$.

Elemental Analysis for: $C_{23}H_{25}FN_2O_3 \cdot HCl \cdot 0.5H_2O$ Calc'd: C, 62.51; H, 6.16; N, 6.34. Found: C, 62.71; H, 5.87; N, 6.50.

The diastereomers of a 120 mg sample of the above compound were separated by preparative chiral HPLC (Chiralpak AD 25×2 cm, ethanol).

Isomer A: $R_T$=16.4 min: N-[(1S*,3S*)-3-(5-fluoro-1H-indol-3-yl)cyclopentyl]-N-{[(2S)-8-methoxy-2,3-dihydro-1,4-benzodioxin-2-yl]methyl}amine was converted to its hydrochloride salt (beige solid): $[\alpha]_D$ −30.01° (c 1.0, MeOH); MS (ESI) m/z 397 [M+H]$^+$.

Isomer B: $R_T$=18.4 min: N-[(1R*,3R*)-3-(5-fluoro-1H-indol-3-yl)cyclopentyl]-N-{[(2S)-8-methoxy-2,3-dihydro-1,4-benzodioxin-2-yl]methyl}amine was converted to its fumarate salt (beige solid): $[\alpha]_D$ −53.00° (c 1.0, MeOH); MS (ESI) m/z 397 [M+H]$^+$.

EXAMPLE 3

N-[(cis)-3-(5-fluoro-1-methyl-1H-indol-3-yl)cyclopentyl]-N-{[(2S)-8-methoxy-2,3-dihydro-1,4-benzodioxin-2-yl]methyl}amine This compound was prepared in a similar manner as Example 1, using cis-3-(5-fluoro-1-methyl-1H-indol-3-yl)-cyclopentylamine to give 0.085 g (19%) of the title compound as its hydrochloride salt: MS (ESI) m/z 411 [M+H]$^+$.

Elemental Analysis for: $C_{24}H_{27}FN_2O_3 \cdot HCl \cdot 0.25H_2O$ Calc'd: C, 63.85; H, 6.36; N, 6.21. Found: C, 63.50; H, 6.33; N, 6.21.

EXAMPLE 4

N-[(trans)-3-(5-fluoro-1-methyl-1H-indol-3-yl)cyclopentyl]-N-{[(2S)-8-methoxy-2,3-dihydro-1,4-benzodioxin-2-yl]methyl}amine This compound was prepared in the same manner as for Example 1, using trans-3-(5-fluoro-1-methyl-1H-indol-3-yl)-cyclopentylamine to give 0.1 g (30%) of the title compound as its hydrochloride salt: MS (ESI) m/z 411 [M+H]$^+$.

Elemental Analysis for: $C_{24}H_{27}FN_2O_3 \cdot HCl \cdot 0.75H_2O$ Calc'd: C, 62.60; H, 6.46; N, 6.08. Found: C, 62.75; H, 6.28; N, 6.17.

EXAMPLE 5

N-{[(2S)-8-thoxy-2,3-dihydro-1,4-benzodioxin-2-yl]methyl}-N-[(cis)-3-(5-fluoro-1H-indol-3-yl)cyclopentyl]amine This compound was prepared in the same manner as for Example 1, using [(2R)-8-ethoxy-2,3-dihydro-benzo[1,4]dioxin-2-yl]methyl 4-methylbenzenesulfonate (0.25 g, 0.68 mmol) and cis-3-(5-fluoro-1H-indol-3-yl)-cyclopentylamine (0.3 g, 1.38 mmol), to afford 0.16 g (64%) of the title compound as its hydrochloride salt: MS (ESI) m/z 411 [M+H]$^+$.

Elemental Analysis for: $C_{24}H_{27}FN_2O_3 \cdot HCl \cdot 0.25H_2O$ Calc'd: C, 63.85; H, 6.36; N, 6.21. Found: C, 63.71; H, 6.24; N, 6.19.

EXAMPLE 6

N-{[(2S)-8-ethoxy-2,3-dihydro-1,4-benzodioxin-2-yl]methyl}-N-[(trans)-3-(5-fluoro-1H-indol-3-yl)cyclopentyl]amine This compound was prepared in the same manner as for Example 1, using [(2R)-8-ethoxy-2,3-dihydro-benzo[1,4]dioxin-2-yl]methyl 4-methylbenzenesulfonate (0.25 g, 0.68 mmol) and trans-3-(5-fluoro-1H-indol-3-yl)-cyclopentylamine (0.3 g, 1.38 mmol) to afford 0.16 g (64%) of the title compound as its hydrochloride salt: MS (ESI) m/z 411 [M+H]$^+$.

Elemental Analysis for: $C_{24}H_{27}FN_2O_3 \cdot HCl \cdot 0.5H_2O$ Calc'd: C, 63.22; H, 6.41; N, 6.14. Found: C, 63.40; H, 6.54; N, 6.28.

EXAMPLE 7

3-[3-({[(2S)-8-methoxy-2,3-dihydro-1,4-benzodioxin-2-yl]methyl}amino)cyclopentyl]-1H-indole-5-carbonitrile To a mixture of [(2S)-8-methoxy-2,3-dihydro-benzo[1,4]dioxin-2-yl]-methylamine (0.18 g, 0.98 mmol), 3-(3-oxo-cyclopentyl)-1H-indole-5-carbonitrile (0.35 g, 1.56 mmol), and glacial acetic acid (0.15 mL) in dichloroethane (10 mL) at room temperature was added sodium triacetoxy borohydride (0.3 g, 1.42 mmol). After stirring at room temperature for 24 h, the mixture was poured in 5% aqueous $NaHCO_3$ solution (50 mL) and extracted with ethyl acetate (2×75 mL). The combined organic layers were washed with water (50 mL) and brine (50 mL), then were dried over anhydrous sodium sulfate, filtered and concentrated to give 0.46 g of crude product. Flash chromatography on $SiO_2$ (5% 2 M $NH_3$ in MeOH/ethyl acetate) afforded 0.12 g (32%) of the (S)-cis isomer (first to elute) and 0.06 g (16%) of the (S)-trans isomer.

Isomer A: 3-[(cis)-3-({[(2S)-8-methoxy-2,3-dihydro-1,4-benzodioxin-2-yl]methyl}amino)-cyclopentyl]-1H-indole-5-carbonitrile was converted to its hydrochloride salt (white solid): MS (ESI) m/z 404 [M+H]$^+$.

Elemental Analysis for: $C_{24}H_{25}N_3O_3 \cdot HCl \cdot 0.25H_2O$ Calc'd: C, 64.86; H, 6.01; N, 9.45. Found: C, 64.72; H, 6.02; N, 9.36.

Isomer B: 3-[(trans)-3-({[(2S)-8-methoxy-2,3-dihydro-1,4-benzodioxin-2-yl]methyl}-amino)cyclopentyl]-1H-indole-5-carbonitrile was converted to its hydrochloride salt: MS (ESI) m/z 404 [M+H]$^+$.

Elemental Analysis for: $C_{24}H_{25}N_3O_3 \cdot HCl \cdot 1.75H_2O$ Calc'd: C, 61.14; H, 6.31; N, 8.19. Found: C, 60.93; H, 5.88; N, 8.77.

EXAMPLE 8

3-[3-({[(2S)-8-methoxy-2,3-dihydro-1,4-benzodioxin-2-yl]methyl}amino)cyclopentyl]-1-methyl-1H-indole-5-carbonitrile This compound was prepared in similar manner as Example 7, using 1-methyl-3-(3-oxo-cyclopentyl)-1H-indole-5-carbonitrile, to give 0.5 g of the crude product. Flash chromatography on $SiO_2$ (5% of 2 M $NH_3$/MeOH in ethyl acetate) afforded 0.43 g of a mixture of isomers. The (S)-cis and (S)-trans isomer were separated by prep HPLC (Primesphere 10 Sil, 5×25 cm, 3% MeOH/$CH_2Cl_2$), affording 0.17 g (40%) of the (S)-cis compound (first to elute) and 0.065 g (15%) of the (S)-trans compound.

Isomer A: 3-[(cis)-3-({[(2S)-8-methoxy-2,3-dihydro-1,4-benzodioxin-2-yl]methyl}amino)-cyclopentyl]-1-methyl-1H-indole-5-carbonitrile was converted to its hydrochloride salt (white solid): MS (ESI) m/z 418 [M+H]$^+$.

Elemental Analysis for: $C_{25}H_{27}N_3O_3 \cdot HCl \cdot 0.75H_2O$ Calc'd: C, 64.23; H, 6.36; N, 8.99. Found: C, 64.30; H, 6.39; N, 8.95.

Isomer B: 3-[(trans)-3-({[(2S)-8-methoxy-2,3-dihydro-1,4-benzodioxin-2-yl]methyl}amino)cyclopentyl]-1-methyl-1H-indole-5-carbonitrile was converted to its hydrochloride salt (white solid): MS (ESI) m/z 418 [M+H]$^+$.

Elemental Analysis for: $C_{25}H_{27}N_3O_3 \cdot HCl \cdot 0.25H_2O$ Calc'd: C, 65.49; H, 6.27; N, 9.17. Found: C, 65.47; H, 6.26; N, 9.16.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of Formula I:

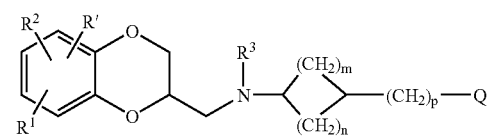

wherein

R$^1$ and R$^2$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or R¹ and R², taken together, form methylenedioxy, ethylenedioxy or propylenedioxy;

R' is halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R³ is hydrogen or alkyl of 1 to 6 carbon atoms;

m is 1 to 3;

n is 1 or 2;

p is 0 to 3 with the proviso that when p is 0, both m and n may not be 2;

Q is a heteroaryl moiety chosen from:

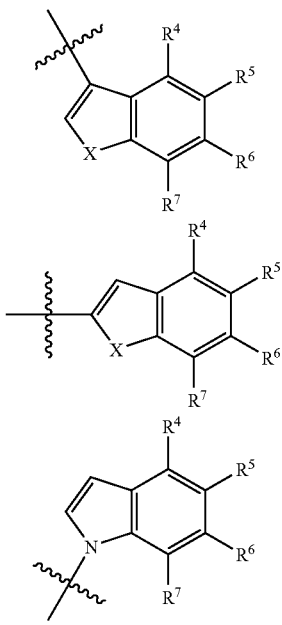

R⁴, R⁵, R⁶ and R⁷ are independently selected from hydrogen, halo, cyano, trifluoromethyl, alkyl of 1 to 6 carbon atoms, alkoxy of 1 to 6 carbon atoms, alkanoyloxy of 2 to 6 carbon atoms;

X is NR⁸; and

R⁸ is hydrogen or alkyl of 1 to 6 carbon atoms;

or a pharmaceutically acceptable salt thereof.

2. A compound according to claim 1, wherein R¹ and R² are, independently, hydrogen, halo, cyano, carboxamido, trifluoromethyl, amino, alkyl of one to six carbon atoms or alkoxy of one to six carbon atoms.

3. A compound according to claim 1, wherein R¹ is alkoxy of one to six carbon atoms and is attached to position 8 of the benzodioxan moiety.

4. A compound according to claim 1, wherein R² is hydrogen.

5. A compound according to claim 1, wherein R⁴, R⁵, R⁶ and R⁷ are independently hydrogen, halo, cyano, alkyl of one to six carbon atoms, or alkoxy of one to six carbon atoms.

6. A compound according to claim 1, wherein R⁴, R⁵, R⁶ and R⁷ are independently hydrogen, halo or cyano.

7. A compound according to claim 1, wherein m and n are, independently 1 or 2.

8. A compound according to claim 1, wherein m is 1 and n is 2.

9. A compound according to claim 1, wherein p is 0 or 1.

10. A compound according to claim 1, wherein p is 0.

11. A compound according to claim 1, wherein R⁸ is hydrogen or alkyl of 1 to 3 carbons.

12. A compound according to claim 1, wherein R³ is hydrogen or alkyl of 1 to 3 carbons.

13. A compound according to claim 1, wherein said compound is N-[(cis)-3-(5-fluoro-1H-indol-3-yl)cyclopentyl]-N-{[(2S)-8-methoxy-2,3-dihydro-1,4-benzodioxin-2-yl]methyl}amine or a pharmaceutically acceptable salt thereof.

14. A compound according to claim 1, wherein said compound is N-[(1R,3S)-3-(5-fluoro-1H-indol-3-yl)cyclopentyl]-N-{[(2S)-8-methoxy-2,3-dihydro-1,4-benzodioxin-2-yl]methyl}amine or a pharmaceutically acceptable salt thereof.

15. A compound according to claim 1, wherein said compound is N-[(1S,3R)-3-(5-fluoro-1H-indol-3-yl)cyclopentyl]-N-{[(2S)-8-methoxy-2,3-dihydro-1,4-benzodioxin-2-yl]methyl}amine or a pharmaceutically acceptable salt thereof.

16. A compound according to claim 1, wherein said compound is N-[(trans)-3-(5-fluoro-1H-indol-3-yl)cyclopentyl]-N-{[(2S)-8-methoxy-2,3-dihydro-1,4-benzodioxin-2-yl]methyl}amine or a pharmaceutically acceptable salt thereof.

17. A compound according to claim 1, wherein said compound is N-[(1S,3S)-3-(5-fluoro-1H-indol-3-yl)cyclopentyl]-N-{[(2S)-8-methoxy-2,3-dihydro-1,4-benzodioxin-2-yl]methyl}amine or a pharmaceutically acceptable salt thereof.

18. A compound according to claim 1, wherein said compound is N-[(1R,3R)-3-(5-fluoro-1H-indol-3-yl)cyclopentyl]-N-{[(2S)-8-methoxy-2,3-dihydro-1,4-benzodioxin-2-yl]methyl}amine or a pharmaceutically acceptable salt thereof.

19. A compound according to claim 1, wherein said compound is N-[(cis)-3-(5-fluoro-1-methyl-1H-indol-3-yl)cyclopentyl]-N-{[(2S)-8-methoxy-2,3-dihydro-1,4-benzodioxin-2-yl]methyl}amine or a pharmaceutically acceptable salt thereof.

20. A compound according to claim 1, wherein said compound is N-[(trans)-3-(5-fluoro-1-methyl-1H-indol-3-yl)cyclopentyl]-N-{[(2S)-8-methoxy-2,3-dihydro-1,4-benzodioxin-2-yl]methyl}amine or a pharmaceutically acceptable salt thereof.

21. A compound according to claim 1, wherein said compound is 3-[(cis)-3-({[(2S)-8-methoxy-2,3-dihydro-1,4-benzodioxin-2-yl]methyl}amino)cyclopentyl]-1H-indole-5-carbonitrile or a pharmaceutically acceptable salt thereof.

22. A compound according to claim 1, wherein said compound is 3-[(trans)-3-({[(2S)-8-methoxy-2,3-dihydro-1,4-benzodioxin-2-yl]methyl}amino)cyclopentyl]-1H-indole-5-carbonitrile or a pharmaceutically acceptable salt thereof.

23. A compound according to claim 1, wherein said compound is 3-[(cis)-3-({[(2S)-8-methoxy-2,3-dihydro-1,4-benzodioxin-2-yl]methyl}amino)cyclopentyl]-1-methyl-1H-indole-5-carbonitrile or a pharmaceutically acceptable salt thereof.

24. A compound according to claim 1, wherein said compound is 3-[(trans)-3-({[(2S)-8-methoxy-2,3-dihydro-1, 4-benzodioxin-2-yl]methyl}amino)cyclopentyl]-1-methyl-1H-indole-5-carbonitrile or a pharmaceutically acceptable salt thereof.

25. A compound according to claim 1, wherein said compound is N-{[(2S)-8-ethoxy-2,3-dihydro-1,4-benzo-dioxin-2-yl]methyl}-N-[(cis)-3-(5-fluoro-1H-indol-3-yl)cyclopentyl]amine or a pharmaceutically acceptable salt thereof.

26. A compound according to claim 1, wherein said compound is N-{[(2S)-8-ethoxy-2,3-dihydro-1,4-benzo-dioxin-2-yl]methyl}-N-[(trans)-3-(5-fluoro-1H-indol-3-yl)cyclopentyl]amine or a pharmaceutically acceptable salt thereof.

27. A pharmaceutical composition, comprising:
an effective amount of a compound according to claim 1 or a pharmaceutically acceptable salt thereof; and
a pharmaceutically acceptable carrier or excipient.

* * * * *